United States Patent
Amit et al.

(10) Patent No.: US 10,274,837 B2
(45) Date of Patent: Apr. 30, 2019

(54) METROLOGY TARGET FOR COMBINED IMAGING AND SCATTEROMETRY METROLOGY

(71) Applicant: KLA-TENCOR CORPORATION, Milpitas, CA (US)

(72) Inventors: Eran Amit, Haifa (IL); Raviv Yohanan, Qiryat Motzkin (IL)

(73) Assignee: KLA-Tencor Corporation, Milpitas, CA (US)

( * ) Notice: Subject to any disclaimer, the term of this patent is extended or adjusted under 35 U.S.C. 154(b) by 777 days.

(21) Appl. No.: 14/621,026

(22) Filed: Feb. 12, 2015

(65) Prior Publication Data

US 2015/0177135 A1  Jun. 25, 2015

Related U.S. Application Data

(63) Continuation of application No. PCT/US2014/040030, filed on May 29, 2014.
(Continued)

(51) Int. Cl.
- *G03F 7/20* (2006.01)
- *G01N 21/47* (2006.01)
- *G01N 21/95* (2006.01)

(52) U.S. Cl.
CPC ......... *G03F 7/70633* (2013.01); *G01N 21/47* (2013.01); *G01N 21/4785* (2013.01);
(Continued)

(58) Field of Classification Search
CPC .. G01B 11/272; G01N 21/4785; G01N 21/47; G01N 21/9501; G01N 2201/12; G01N 2201/02
See application file for complete search history.

(56) References Cited

U.S. PATENT DOCUMENTS 7,230,705 B1 * 6/2007 Yang .................. G03F 7/70633
257/797
7,671,990 B1  3/2010 Adel et al.
(Continued)

FOREIGN PATENT DOCUMENTS

WO  2014005828 A1  1/2014
WO  2014039689 A1  3/2014
(Continued)

OTHER PUBLICATIONS

Heather J. Patrick et al., "Scatterfield microscopy using back focal plane imaging with an engineered illumination field"; Metrogogy, Inspection and Process Control for Microlithography XX, CN. Archie, Editor, Proc. SPIE 6152 (2006). US.
(Continued)

*Primary Examiner* — Michael Jung
(74) *Attorney, Agent, or Firm* — Suiter Swantz pc llo

(57) ABSTRACT

Metrology targets, design files, and design and production methods thereof are provided. The targets comprise two or more parallel periodic structures at respective layers, wherein a predetermined offset is introduced between the periodic structures, for example, opposite offsets at different parts of a target. Quality metrics are designed to estimate the unintentional overlay from measurements of a same metrology parameter by two or more alternative measurement algorithms. Target parameters are configured to enable both imaging and scatterometry measurements and enhance the metrology measurements by the use of both methods on the same targets. Imaging and scatterometry target parts may share elements or have common element dimensions. Imaging and scatterometry target parts may be combined into a single target area or may be integrated into a hybrid target using a specified geometric arrangement.

18 Claims, 15 Drawing Sheets

Related U.S. Application Data

(60) Provisional application No. 61/977,075, filed on Apr. 8, 2014, provisional application No. 61/830,729, filed on Jun. 4, 2013, provisional application No. 61/829,139, filed on May 30, 2013.

(52) U.S. Cl.
CPC ..... *G01N 21/9501* (2013.01); *G03F 7/70683* (2013.01); *G01N 2201/02* (2013.01); *G01N 2201/12* (2013.01)

(56) References Cited

U.S. PATENT DOCUMENTS

| | | | |
|---|---|---|---|
| 7,804,994 B2 | 9/2010 | Adel et al. | |
| 7,876,438 B2 | 1/2011 | Ghinovker et al. | |
| 7,933,016 B2 | 4/2011 | Mieher et al. | |
| 7,940,386 B1* | 5/2011 | Bevis | G01N 21/4785 356/243.4 |
| 8,035,824 B2 | 10/2011 | Ausschnitt | |
| 8,363,218 B2 | 1/2013 | Den Boef | |
| 8,441,639 B2 | 5/2013 | Kandel et al. | |
| 8,709,687 B2 | 4/2014 | Van Der Schaar et al. | |
| 9,329,033 B2 | 5/2016 | Amit et al. | |
| 2002/0158193 A1* | 10/2002 | Sezginer | G03F 7/70633 250/237 G |
| 2003/0160163 A1 | 8/2003 | Wong et al. | |
| 2004/0066517 A1* | 4/2004 | Huang | G01N 21/956 356/509 |
| 2004/0169861 A1* | 9/2004 | Mieher | G01N 21/956 356/400 |
| 2004/0257571 A1 | 12/2004 | Mieher et al. | |
| 2005/0012928 A1* | 1/2005 | Sezginer | G01B 11/26 356/401 |
| 2005/0195398 A1* | 9/2005 | Adel | B82Y 10/00 356/401 |
| 2006/0033921 A1* | 2/2006 | Den Boef | G03F 7/70341 356/446 |
| 2006/0117293 A1* | 6/2006 | Smith | G03F 7/70633 716/50 |
| 2007/0108368 A1* | 5/2007 | Mieher | B22D 11/064 250/201.2 |
| 2007/0229829 A1* | 10/2007 | Kandel | G03F 7/70633 356/401 |
| 2007/0229837 A1* | 10/2007 | Schaar | G03F 7/70483 356/456 |
| 2008/0142998 A1* | 6/2008 | Silver | H01L 23/544 257/797 |
| 2009/0262362 A1 | 10/2009 | De Groot et al. | |
| 2011/0304851 A1 | 12/2011 | Coene et al. | |
| 2013/0035888 A1 | 2/2013 | Kandel et al. | |
| 2013/0100427 A1 | 4/2013 | Koolen et al. | |
| 2013/0208279 A1 | 8/2013 | Smith | |
| 2013/0258310 A1 | 10/2013 | Smilde et al. | |
| 2014/0060148 A1 | 3/2014 | Amit et al. | |
| 2014/0111791 A1 | 4/2014 | Manassen et al. | |
| 2014/0139815 A1 | 5/2014 | Amir | |

FOREIGN PATENT DOCUMENTS

| | | |
|---|---|---|
| WO | 2014062972 A1 | 4/2014 |
| WO | 2014074893 A1 | 5/2014 |

OTHER PUBLICATIONS

Hsu-Ting Huang et al. "Scatterometry-Based Overlay Metrology"; Metrology, Inspection, and Process Control for Microlithography XVII, Daniel J. Herr, Editor, Proceedings of SPIE vol. 5038 (2003).

Chui-Fu Chiu et al.; "Towards Faster and Better Litho Control in High Volume Manufacturing" Metrology, Inspection, and Process Control for Microlithography XXVI, edited by Alexander Starikov, Proc. of SPIE vol. 8324, 832426 (2012).

Heather J. Patrick et al.; "Scatterfield Microscopy Using Back Focal Plane Imaging With an Engineered Illumiation Field", Metrology, Inspection, and Process Control for Microlithography XX, C.N. Archie, Editor, Proc. SPIE 6152 (2006).

\* cited by examiner

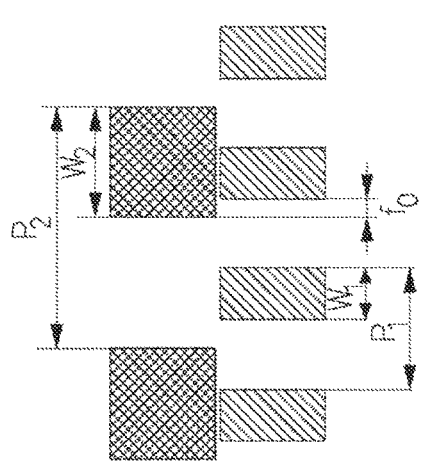
Figure 10B
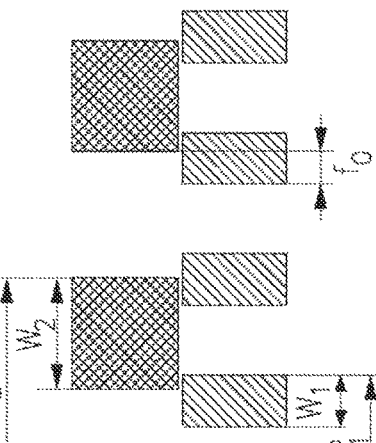
Figure 10C
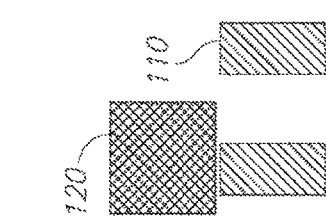
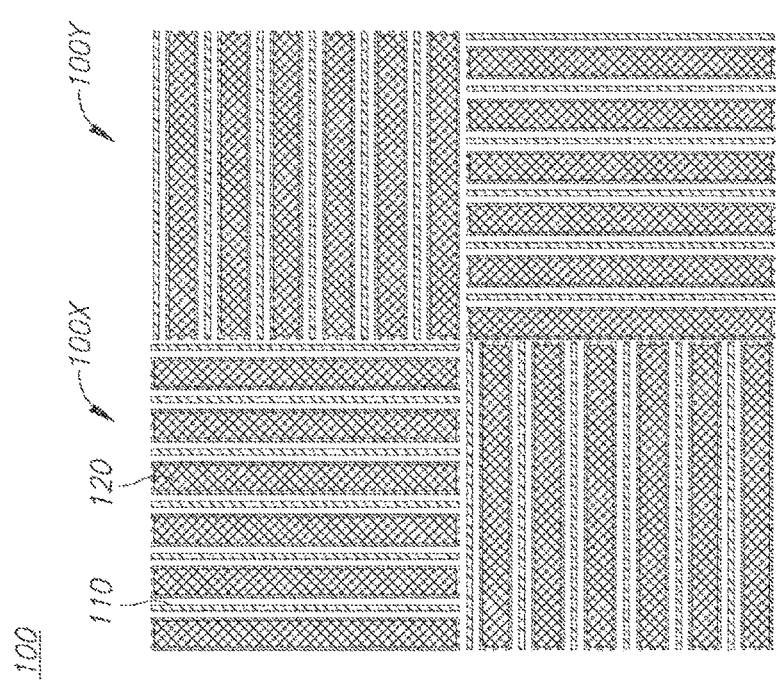
Figure 10A

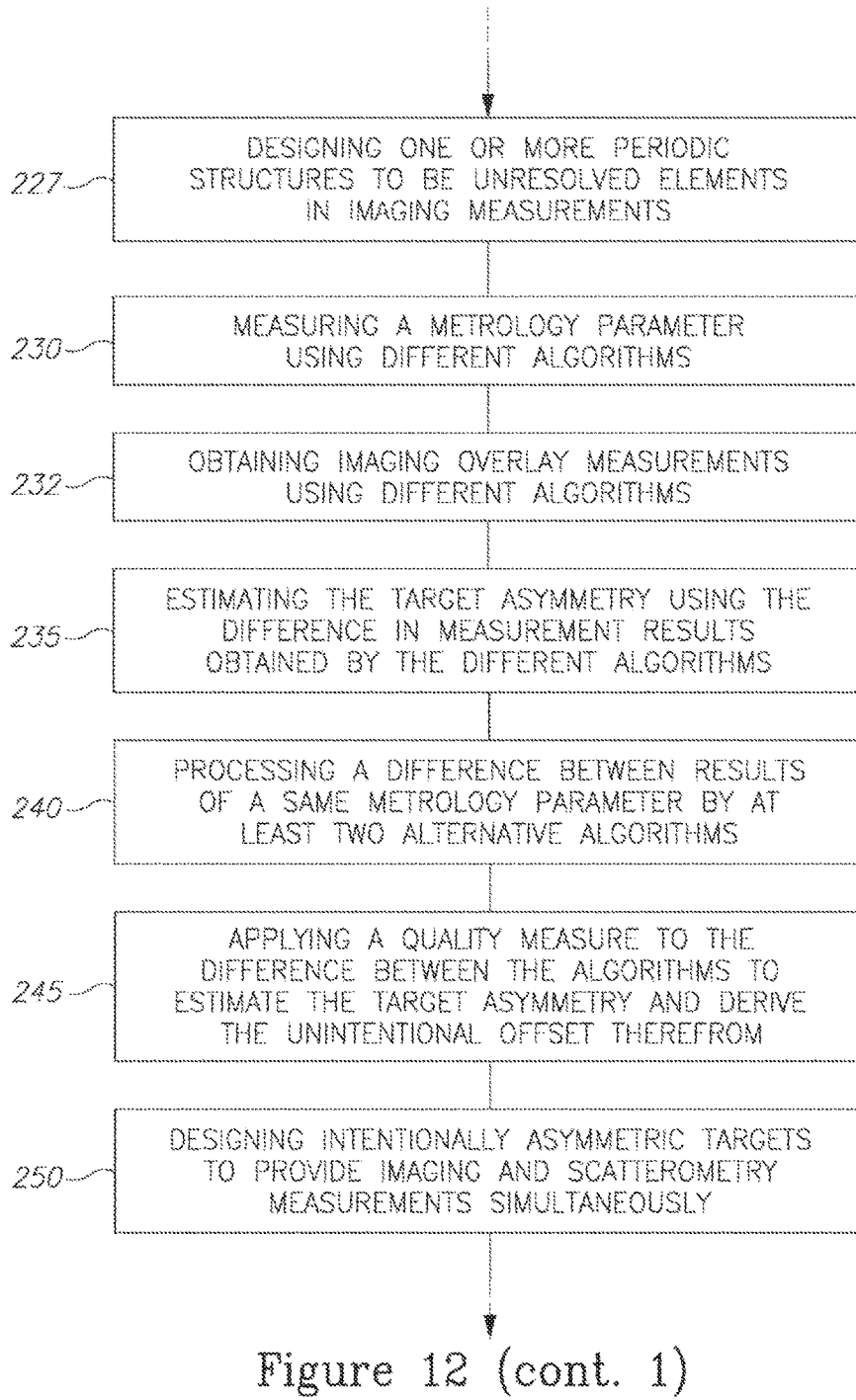
Figure 12 (cont. 1)

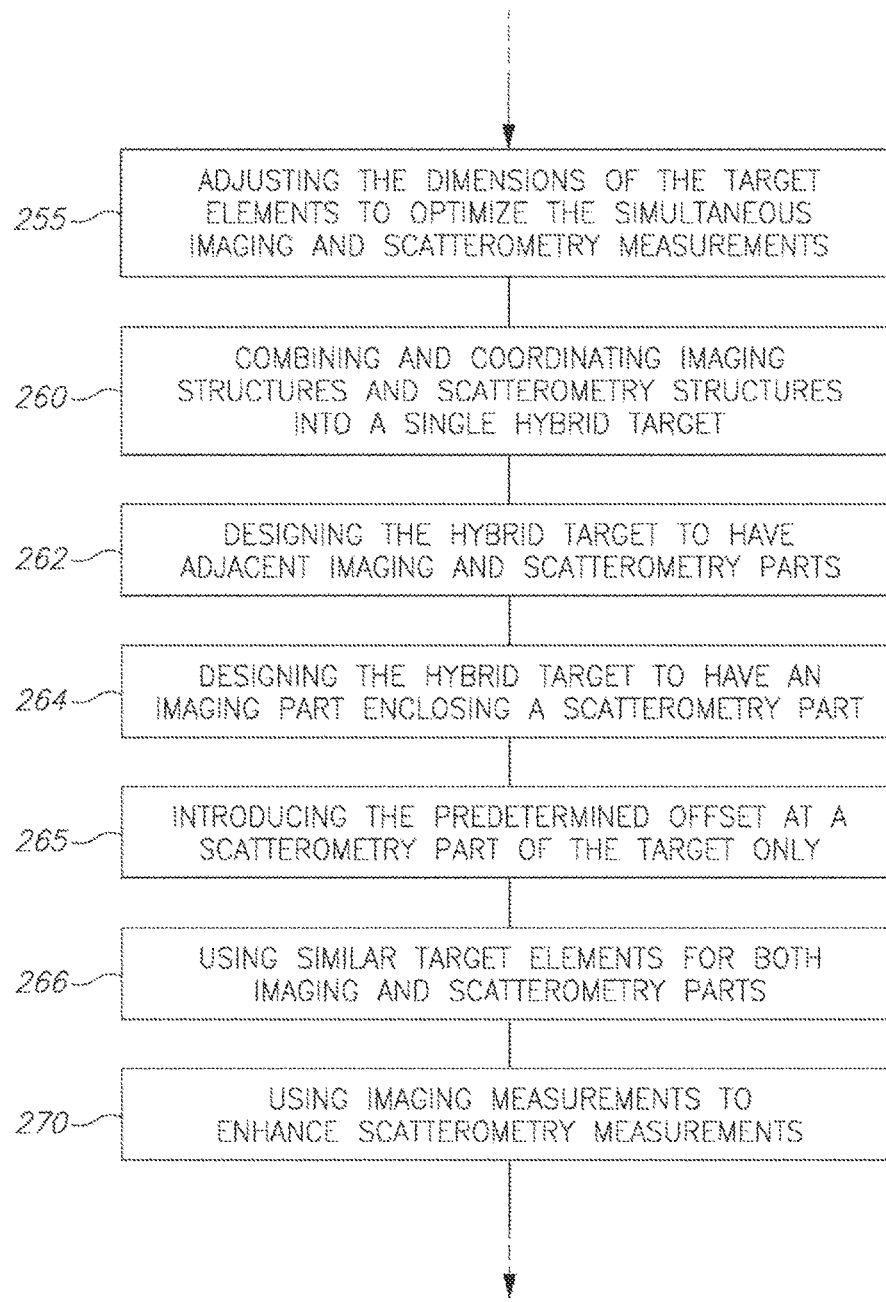
Figure 12 (cont. 2)

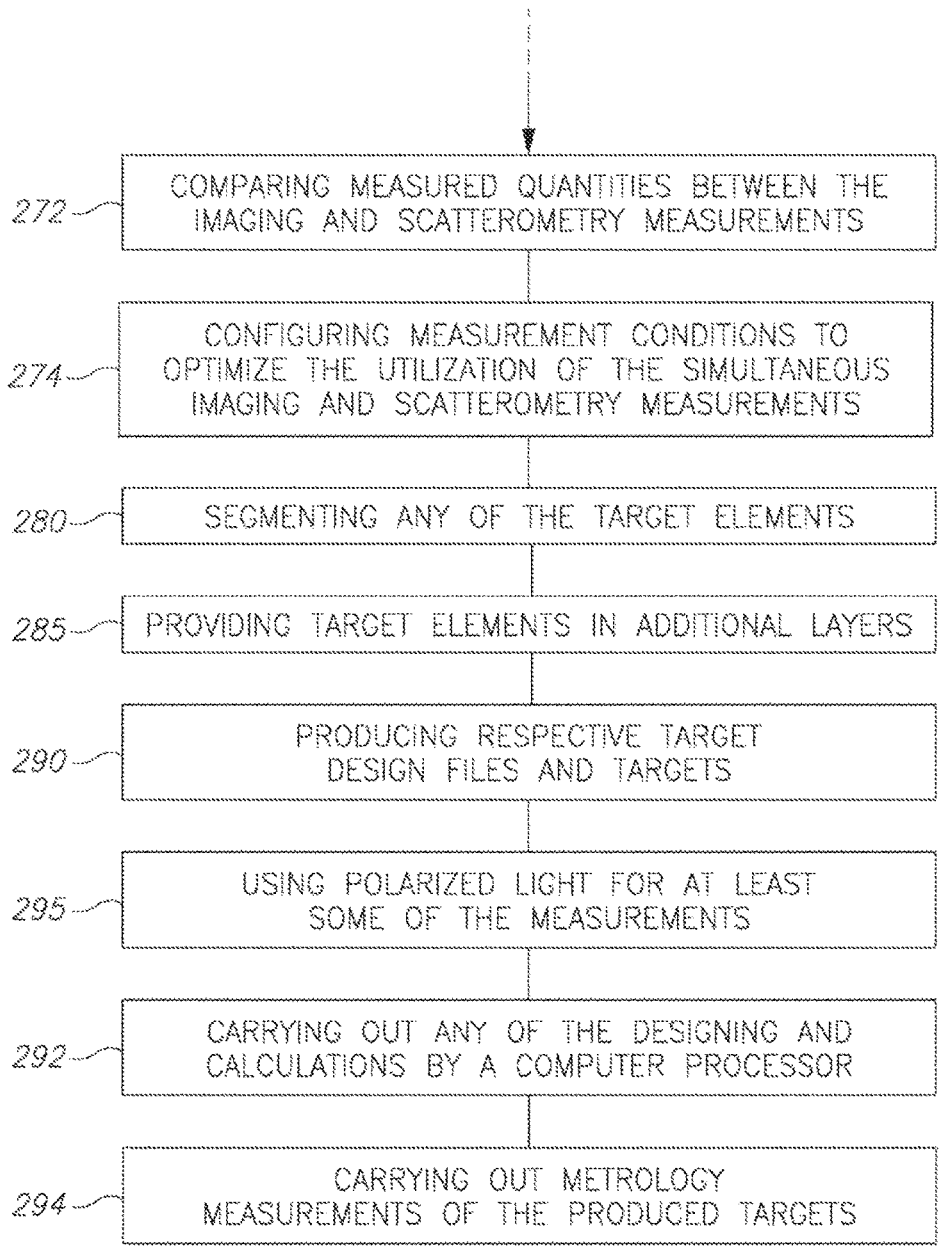
Figure 12 (cont. 3)

METROLOGY TARGET FOR COMBINED IMAGING AND SCATTEROMETRY METROLOGY

CROSS-REFERENCE TO RELATED APPLICATIONS

This application is filed under 35 U.S.C. § 120 and § 365(c) as a continuation of International Patent Application Serial No. PCT/US14/40030, filed on May 29, 2014, which application claims the benefit under 35 U.S.C. 119(e) of U.S. Provisional Patent Application No. 61/829,139, filed on May 30, 2013, U.S. Provisional Patent Application No. 61/830,729, filed on Jun. 4, 2013, and U.S. Provisional Patent Application No. 61/977,075, filed on Apr. 8, 2014, which applications are incorporated herein by reference.

FIELD OF THE INVENTION

The present invention relates to the field of metrology targets, and more particularly, to metrology targets for combined imaging and scatterometry measurements.

BACKGROUND OF THE INVENTION

Metrology targets are designed to enable the measurement of parameters that indicate the quality of wafer production steps and quantify the correspondence between design and implementation of structures on the wafer. Imaging metrology targets as specific structures optimize the requirements for device similarity and for optical image measurability and their images provide measurement data. Scatterometry metrology targets on the other hand, yield diffraction patterns at the pupil plane, from which target parameters may be derived.

BRIEF SUMMARY OF THE INVENTION

One aspect of the present invention provides a metrology target comprising at least two parallel periodic structures at respective layers, wherein a predetermined offset is introduced between the periodic structures.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. In the accompanying drawings:

FIG. 10A is a high level schematic illustration of metrology targets, according to some embodiments of the invention;

FIG. 10B is a high level schematic illustration of metrology targets, according to some embodiments of the invention;

FIG. 10C is a high level schematic illustration of metrology targets, according to some embodiments of the invention;

DETAILED DESCRIPTION OF THE INVENTION

Figure 1:
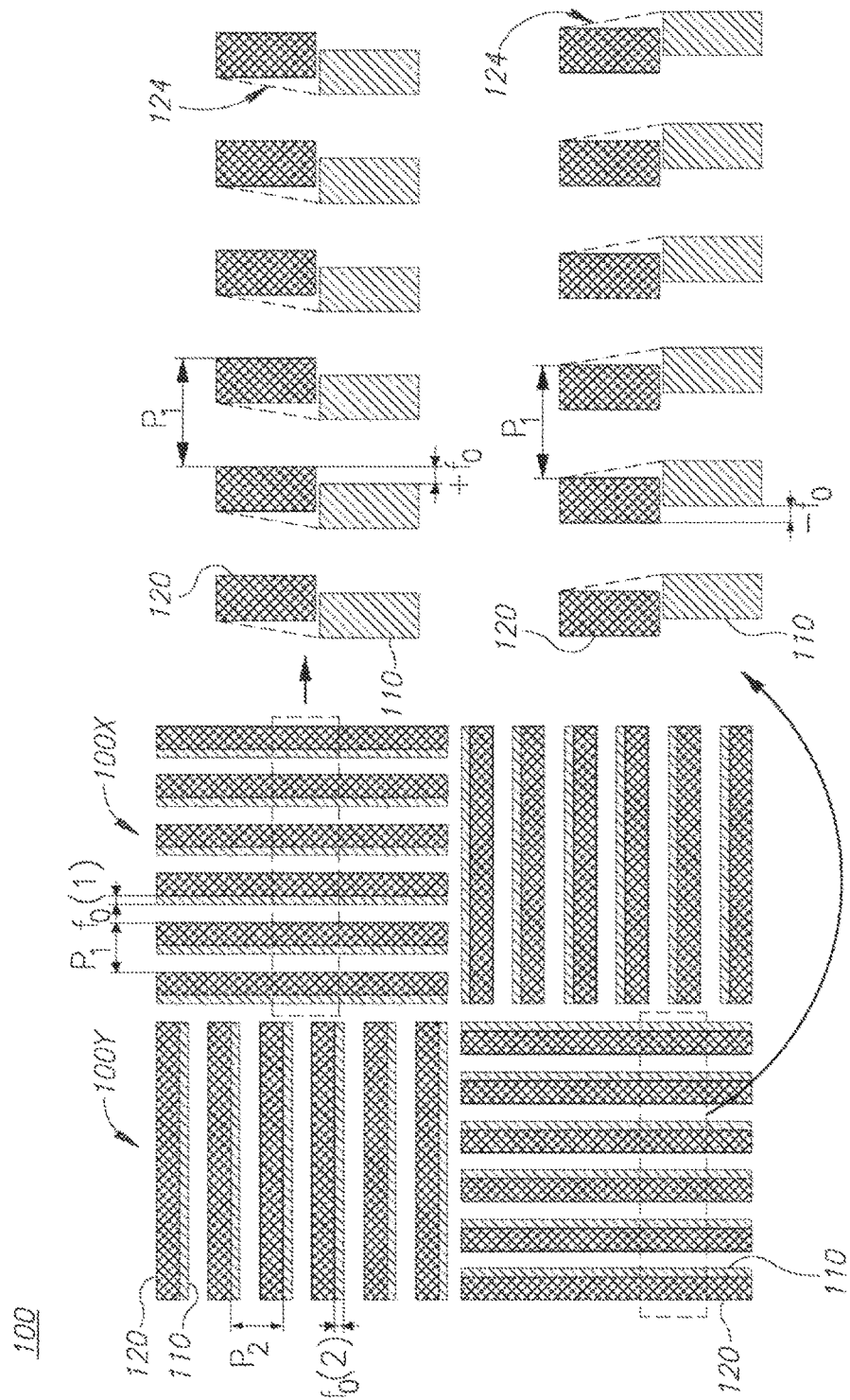
FIG. 1 is a high level schematic illustration of metrology targets, according to some embodiments of the invention.

Prior to the detailed description being set forth, it may be helpful to set forth definitions of certain terms that will be used hereinafter.

The terms "metrology target" or "target" as used herein in this application, are defined as structures designed or produced on a wafer which is used for metrological purposes. The term "layer" as used herein in this application, is defined as any of the layers used in a photolithography process in any of its steps. The term "layer" as used herein in this application, may comprise different patterns on the same physical layer, which are created in different processes or lithography steps.

The term "periodic structure" as used in this application refers to any kind of designed or produced structure in at least one layer which exhibits some periodicity. Periodic structures at different layers may be configured to yield target elements which are not periodic within the measurement resolution, e.g., when structure elements are not resolved under specific measurement conditions. The periodicity of periodic structures is characterized by its pitch, namely its spatial frequency. For example, a bar as a target element may be produced as a group of spaced parallel lines, thereby reducing the minimal feature size of the element and avoiding monotonous regions in the target. Each element of a periodic structure is referred to as a target element.

The term "target element" as used herein in this application, is defined as a feature in the metrology target such as individual target areas or boxes, grating bars etc. Target elements may be full or empty (gaps), and may also be segmented, i.e., may comprise multiple smaller features which cumulatively constitute the target element. A target and/or a periodic structure is referred to as comprising target elements, each "target element" being a feature of the target that is to be distinguished from its background, the "background" being a wafer area proximate to a target element on the same or on a different layer (above or below the target element). The term "crosstalk" as used herein in this application, is defined as optical interaction between signals from different target elements, such as optical interaction between parallel periodic structures at different layers.

The term "offset" as used herein in this application, is defined as a shift between target elements at different layers, which is intended and predetermined. The term "overlay" as used herein in this application, is defined as a shift between layers which includes an unintentional component (e.g., due to process inaccuracies) that may cause production inaccuracies and is thus aim of a metrology measurement. The measured or simulated overlay (OVL) may comprise donations from a predetermined offset component and from an unintentional overlay inaccuracy.

The terms "quality merit", "quality metric", "quality measure" and "Qmerit" are used herein throughout this application to refer to a mathematical transformation of measurement results into one or more figures of merit which may serve as metrics to characterize metrology parameters (e.g., overlay measurements).

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments of or being practiced or carried out in various ways. Also, it is to be understood that the phraseology and terminology employed herein is for the purpose of description and should not be regarded as limiting.

Metrology targets, design files, and design and production methods thereof are provided. The targets comprise two or more parallel periodic structures at respective layers, wherein a predetermined offset is introduced between the periodic structures. Target parameters are configured to enable both imaging and scatterometry measurements and enhance the metrology measurements by the use of both methods on the same targets. Imaging and scatterometry target parts may share elements or have common element dimensions. Imaging and scatterometry target parts may be combined into a single target area or may be integrated into a hybrid target using a specified geometric arrangement.

Figure 3:
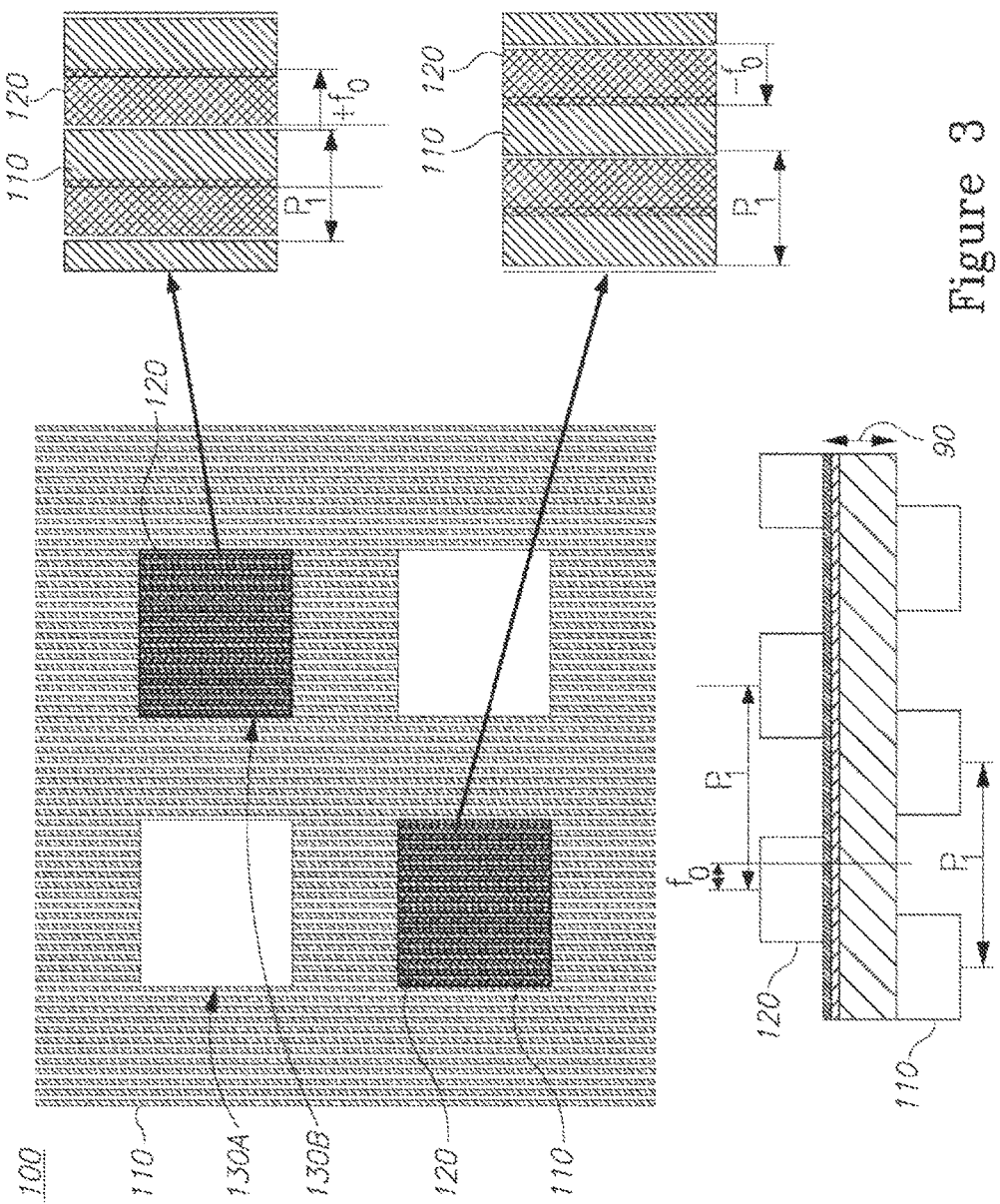
FIG. 3 is a high level schematic illustration of metrology targets, according to some embodiments of the invention.

FIGS. 1 and 3 are high level schematic illustrations of metrology targets 100, according to some embodiments of the invention. The left side of FIG. 1 schematically illustrates a top view of target 100, having four cells (quarters of target 100 in the non-limiting illustration), two cells 100X configured to enable metrology measurements in one direction (arbitrarily designated by X) and two cells 100Y configured to enable metrology measurements in another direction (arbitrarily designated by Y), in the non-limiting example—Y being perpendicular to X. The right side of FIG. 1 schematically illustrates cross sectional side views of two segments of cells 100X target 100. Target 100 is illustrated, in a non-limiting manner, as having two layers, a bottom previous layer with periodic structure 110 and a top current layer with periodic structure 120. These layers may represent any number of target layers and may be interspaced by any number of intermediate layers 90 (shown schematically in FIG. 3). Periodic structures 110, 120 may have identical pitches at regions in which they are parallel. The pitches may differ between measurement directions and/or between target cells. For example, periodic structures 110, 120 may have a first pitch $p_1$ in cells 100X and a second pitch $p_2$ in cells 100Y. Pitches $p_1$, $p_2$ may be for example selected in the range 0.5-1.5 µm. The pitches may be determined according to metrology and process compatibility requirements. Specific hardware of the metrology tool (e.g., short illumination wavelength, bigger effective objective NA (numerical aperture), polarized illumination and\or collection light) may be used to measure targets with smaller pitches. Predetermined offsets $f_0$ may be about 5-30 nm for substantially overlapping periodic structures. Periodic structures 110, 120 may be shifted by half pitch, quarter pitch, or any other fraction of the pitch with respect to each other (center of top lay bar above center of bottom layer space), and in such cases offset $\pm f_0$ may be defined as shifts with respect to the shifted structures.

Different offsets may be introduced in different parts of target 100, for example opposite offsets may be set at different, optionally corresponding or paired parts of target 100 such as periodic structures measured in the same measurement direction. In certain embodiments, the opposite predetermined offsets add differently to unintentional overlays and thus allow extracting the unintentional overlays. Using imaging metrology techniques as a non-limiting example, the unintentional overlay may be estimated using differences in overlay measurements by different algorithms. A metrology parameter may be measured using different algorithms (e.g., imaging overlay measurements may be obtained using different algorithms) and the target asymmetry may be estimated using the difference in measurement results obtained by the different algorithms, for example, by processing a difference between results of a same metrology parameter by the alternative algorithms or generally by applying a quality measure to the difference between the algorithms to estimate the target asymmetry and derive the unintentional offset therefrom. Respective target designs and measurement algorithms are thus disclosed herein. In certain embodiments, the difference between the results by different algorithms may be proportional to the unintentional offset, as measurements for target parts with opposite predetermined offsets may be subtracted from each other to express the difference only in terms of the unintentional offset.

While FIGS. 1 and 3 represent target designs which are typically measured by scatterometry techniques, these designs may be modified to be measurable by imaging techniques.

In certain embodiments, one of periodic structures 110, 120 may be not periodic (see e.g., target elements 130A, 130B in FIG. 11 below) or be segmented with pitch as small as the process allows (e.g., minimal device pitch). In the latter case, target elements in different layers may have different segmentation pitches. The predetermined offset may be defined by the offsets between edges of the respective elements or by edges of the respective layers, as is explained below in more details with respect to the unresolved measurements.

In certain embodiments, parameters of periodic structures 110, 120 may be selected to optimize measurement conditions for both imaging and scatterometry methods. For example, periodic structures 110, 120 may be larger than customary for scatterometry measurements, but still achieve sufficient measurement precision. In a non-limiting example, periodic structure pitch may be larger than 1200 nm to enable both resolution and sufficient measurement data collection. In another example, features of periodic structures 110, 120 may be unresolved (e.g., have pitches much smaller than half the illumination wavelength) for imaging measurements in one measurement direction but still provide enough useful information to enhance the corresponding scatterometry measurements (see e.g., FIG. 3 below). In certain embodiments, imaging and/or scatterometry measurements may be carried out in polarized light to enhance measurement resolution with respect to any relevant targets 100. In certain embodiments, metrology measurements of targets 100 may be carried out while attenuating or blocking a zero order reflection for at least some of the measurements, to enhance overlay detection using imaging or scatterometry.

Metrology target 100 comprises at least two parallel periodic structures 110, 120 at respective layers. A predetermined offset $f_0$ is introduced between periodic structures 110, 120, and target 100 is hence made to be at least partially asymmetric. Target parameters may be configured to enable both imaging and scatterometry measurements.

Parallel periodic structures 110, 120 may be arranged in pairs of target cells, and the predetermined offsets that are introduced between the periodic structures may be opposite in direction in the cells of the at least one pair. In the non-limiting illustration of FIG. 1, opposite predetermined offsets $f_0$ are introduced in the two cells in each direction ($+f_0(1)$ and $-f_0(1)$ in cells 100X as illustrated in the cross sections; $+f_0(2)$ and $-f_0(2)$ in cells 100Y). Predetermined offsets $f_0$ may vary between the measurement directions.

Target 100 may comprise any number of target layers with respective periodic structures and any number of intermediate layers 90, according to target design and metrology considerations.

Parallel periodic structures 110, 120 may be partially or mostly overlapping, as illustrated e.g., in FIG. 1, or parallel periodic structures 110, 120 may be mostly or wholly non-overlapping, as illustrated e.g., in FIG. 3. In either case, but particularly in the latter case, any of periodic structures 110, 120 may be unresolved with respect to imaging metrology measurements. The central part of FIG. 3 schematically illustrates a top view of target 100, having four cells, two of which configured to enable scatterometry and imaging measurements in one direction (similar to FIG. 1). The right part of FIG. 3 schematically illustrates enlarged top views of the target cells, while the bottom part of FIG. 3 schematically illustrates a cross section of parallel periodic structures 110, 120. Opposite predetermined offsets $f_0$ are introduced in the two target cells. As schematically illustrated, periodic structure 110 may extend over a larger area of target 100, beyond the cells occupied by parallel periodic structure 120. It is noted that the sizes of targets elements in periodic structures 110, 120 are not limiting and merely serve illustrative purposes. In an example for unresolved measurements, periodic structure 110, 120 may be configured to represent a continuous target element (under a given resolution), similar to target elements 130A, 130B schematically illustrated in FIG. 11 below. In this respect, composite elements are denoted by 130A, 130B in FIG. 3 as well. Imaging measurements of target 100 illustrated in FIG. 3 may comprise only measuring the right and left element edges of target elements 130A, 130B imaged as full square targets. In certain embodiments, pitch $p_1$ may be made too small to enable scatterometry overlay measurements. Another option is to use imaging technology to measure the two empty squares (target elements 130A) versus the two full squares (target elements 130B) of the current layer. Such imaging measurements may suffice on their own and/or to complement the scatterometry measurements. Furthermore, different imaging measurement algorithms may be used in two direction measurements of the respective feature. Taking as a non-limiting example the upper right square in FIG. 3, periodic structure 120 may have a pitch that is unresolved along the x direction, but having a target element length that enables measurement in the y direction. Figures of merit discussed below may be used to measure the symmetry breaking for both resolved and unresolved structure. In certain embodiments, targets 100 may comprise at least one of periodic structures 110, 120 which is unresolved under specified measurement conditions and/or at least one of periodic structures 110, 120 which comprises a single target element.

The inventors suggest that under certain measurement conditions, the introduced predetermined offset may have an effect on metrology measurements that is similar to the effect of a side wall angle, for example, similar to line 124 illustrated in FIG. 1. The inventors have found out that crosstalk between target layers, i.e., optical interaction between respective illumination and measured signals from the layers, may result in such similarity, which may then be used to algorithmically calculate the overlay. It is noted that such apparent side wall angle effect may depend on the direction of illumination, as target 100 is asymmetric due to the introduced predetermined offset.

Comparing line 124 in the top and bottom side views on the right side of FIG. 1, it is noted that the angle of each feature edge may be designed to be identical. The overlap between the layers may be described as a change of this edge angle. This effective angle shift should be zero when the overlay is zero or half pitch. Upon introducing a small horizontal overlay $f_0$, the angle shift of the left edge should be the opposite of the right edge shift. In addition, the angle shift should be anti-symmetric: If the overlay is $-f_0$, the new shift of the right edge should be the same shift of the left edge when there is overlay $+f_0$. Moreover, the shift of the left edge of the bottom left feature should be the same as the shift of the right edge of the top right feature. Any deviation from such anti-symmetric angle shifts may be used to calculate the unintentional component of the overlay.

The Overlay (OVL) values calculated using imaging and scatterometry may be used as quality merit for the measurement and target or as basis for calculating such quality merits. If the overlay values measured by imaging and scatterometry do not match, target 100 may be identified as being produced at low quality. In certain embodiments, weighted OVL values of imaging and scatterometry measurement techniques may be used, either to report one weighted OVL value per target or to derive a weighted OVL model. In certain embodiments, the OVL values of one technique and quality merits measured using the second technique may be used in combination. The combination of the information from both techniques may yield better unified quality merits and may provide additional geometrical information regarding the printed target. In certain embodiments, measurement results by one technology may be used to calibrate the second technology OVL values (for example, if one technique is measured faster but less accurately than the other). In general, in any of the embodiments, measurement technique, processing of the results and user data may be selected according to requirements.

In certain embodiments, imaging overlay may be calculated using algorithms adapted to target features such as a side wall angle, for example algorithms along the lines taught by U.S. Patent Publication No. 2013/0035888. In particular, such or similar algorithms may be used to estimate the degree of target asymmetry introduced by the predetermined offsets. For example, the measure termed Qmerit (which may be, for example, the difference between some pre-defined OVL algorithms applied on the same image) described in U.S. Patent Publication No. 2013/0035888 was found to be proportional to this angle shift. U.S. Patent Publication No. 2013/0035888, which is incorporated herein by reference in its entirety, discloses acquiring a plurality of overlay metrology measurement signals from a plurality of metrology targets distributed across one or more fields of a wafer of a lot of wafers, determining a plurality of overlay estimates for each of the plurality of overlay metrology measurement signals using a plurality of overlay algorithms, generating a plurality of overlay estimate distributions, and generating a first plurality of quality metrics utilizing the generated plurality of overlay estimate distributions, wherein each quality metric corresponds with one overlay estimate distribution of the generated plurality of overlay estimate distributions, each quality metric being a function of a width of a corresponding generated overlay estimate distribution, each quality metric further being a function of asymmetry present in an overlay metrology measurement signal from an associated metrology target. Furthermore, U.S. Patent Publication No. 2013/0035888 discloses determining a first process signature as a function of position across the wafer by comparing a first set of metrology results acquired from the plurality of proxy targets following a lithography process and prior to a first etching process of the wafer and at least a second set of metrology results acquired from the plurality of proxy targets following the first etching process of the wafer; correlating the first process signature with a specific process path; measuring a device correlation bias following the first etching process by performing a first set of metrology measurements on the plurality of device correlation targets of the wafer, the device correlation bias being the bias between a metrology structure and a device of the wafer; determining an additional etch signature for each additional process layer and for each additional non-lithographic process path of the wafer as a function of position across the wafer; measuring an additional device correlation bias following each additional process layer and each additional non-lithographic process path of the wafer; and generating a process signature map database utilizing the determined first etch signature and each of the additional etch signatures and the first measured device correlation bias and each additional device correlation bias, for example, the comparing may comprise determining a difference between a first set of metrology results acquired from the plurality of proxy targets following a lithography process and prior to a first etching process of the wafer and at least a second set of metrology results acquired from the plurality of proxy targets following the first etching process of the wafer. Any of the embodiments of the quality metric disclosed by U.S. Patent Publication No. 2013/0035888 may be used in certain embodiments of the current invention, and is referred to in the following by the term "Qmerit". In certain embodiments of the current invention, the quality metric referred to as "Qmerit" may be used to derive a measure of target asymmetry by comparing results of different algorithms applied to the same target.

The inventors have found out, that while symmetric targets (lacking the predetermined offsets) result in essentially similar measurements by different measurement algorithms (i.e., different algorithms yield the same results with differing levels of precision), the disclosed asymmetric targets yield differences in measurement results by different algorithms, because the asymmetry affects different algorithms in different ways. Certain embodiments of the current invention utilize these differences, e.g., via application of Qmerit, to extract the overlay, and in particular the unintentional offset, from the differences between measurement results of the asymmetric targets by different algorithms. In a non-limiting example, overlay measurements of disclosed asymmetric targets by different imaging algorithms (e.g., algorithms calculating average intensities, algorithms calculating weighted averages, edge detection algorithms, algorithms calculating cross-correlations across the target and other image processing algorithms) yields differences between target parts having different asymmetries, which are used to extract the unintentional component of the overlay. For example, in FIG. 1, the top left and the bottom right quarters of target 100 exhibit opposite predetermined offsets $f_0$, which combine differently with an unintentional offset to yield the differences between different algorithms in measuring the overlay. In certain embodiments, metrology measurements target 100 may further comprise deriving information regarding process and target quality and defects by combining overlay values and quality merits of both imaging and scatterometry measurements. Process monitoring and process control may be enhanced by using such derived additional information.

Figure 2B:
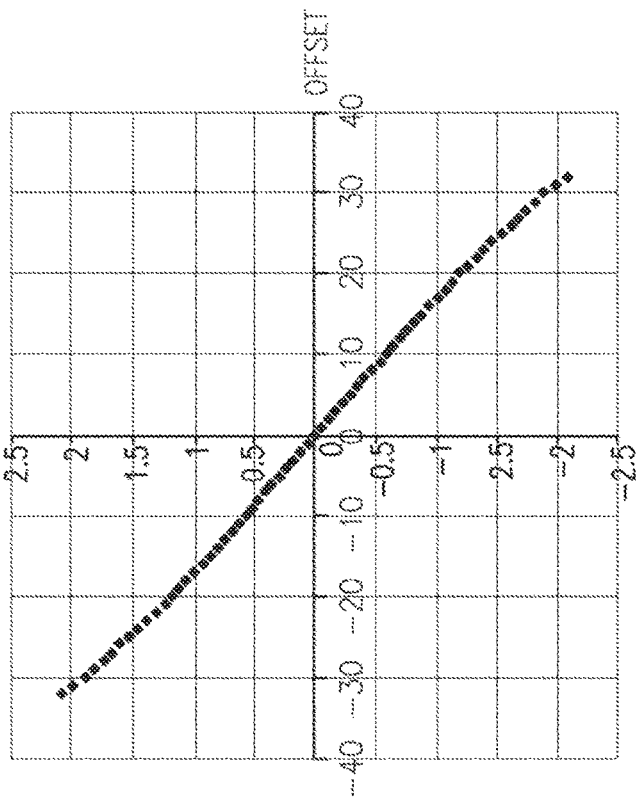
FIG. 2B is a schematic illustration of the efficiency of the proposed targets and measurement methods, according to some embodiments of the invention.
Figure 2A:
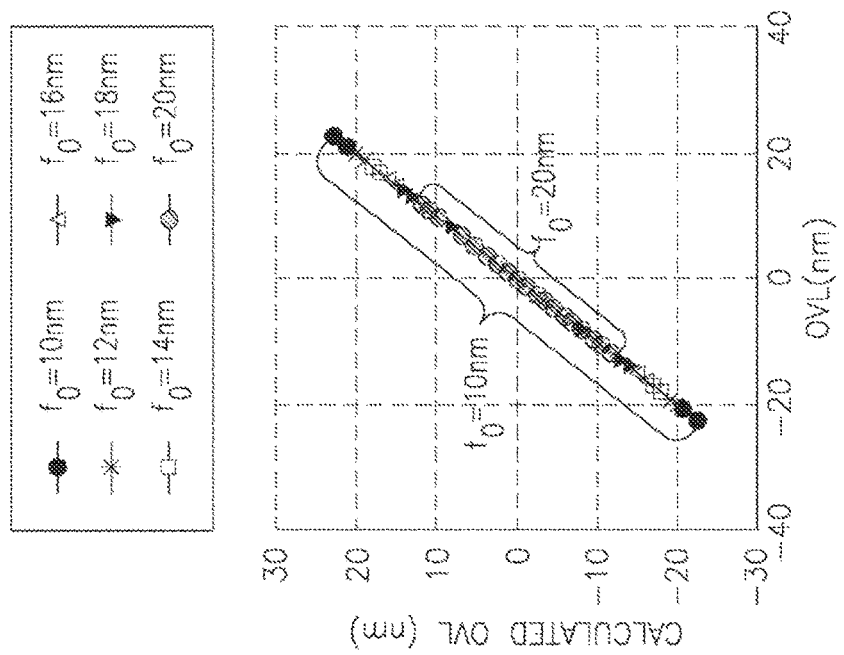
FIG. 2A is a schematic illustration of the efficiency of the proposed targets and measurement methods, according to some embodiments of the invention.

FIGS. 2A and 2B schematically illustrate a simulation-based efficiency of the proposed targets and measurement methods, according to some embodiments of the invention. FIG. 2A compares the calculated overlay with respect to the real overlay, for a range of predetermined offsets $f_0$ between 10-20 nm in simulation results with illumination wavelength of 750 nm. It is noted that larger offsets allow for a narrower range of overlays because in the simulation the maximal overlay was fixed. The inventors have found out that the calculated overlays are identical to the real overlays. Similar results were found for a range of illumination wavelengths between 600-800 nm. FIG. 2B illustrates the anti-symmetric relation between the Qmerit measure of the offset and the actual offset, indicating that this and similar measures may be effectively used to reliably measure overlays in targets 100. The inventors have further found out that targets 100 produce measurements which are sufficiently sensitive for scatterometry purposes. The anti-symmetric relation between the Qmerit measure and the offset $f_0$ may be used to calculate the overlay using the formula:

$$OVL = f_0 \frac{Qmerit(f_0) + Qmerit(-f_0)}{Qmerit(f_0) - Qmerit(-f_0)} \qquad \text{Equation 1}$$

with Qmerit($\pm f_0$) being Qmerit of the cell with intended shift of $\pm f_0$. Equation 1 is a simple way to connect the overlay with the chosen figure of merit, and merely serves as a non-limiting in example for such relations, which may be formulated in more complex ways.

In order to estimate the OVL along the x axis of targets 100 of FIG. 3, the Qmerit values of each layer and of any feature may be used. If the two Qmerit values of a layer are below precision then the crosstalk-induced overlay error can be neglected; for this layer (and measurement conditions) layer crosstalk should not be of concern and the standard imaging algorithm can be used. If the crosstalk is not negligible it can be calculated using Equation 1. In certain embodiments, target 100 may be modified to allow regular overlay calculation using, e.g., the top right and the bottom left quarters. Another method for accurate overlay calculation is calculating the x center of the current top right and bottom left features in addition to the Qmerit. This value can be compared to the x center calculated using the current top right and bottom left features. Assuming that calculations for both centers should give the same value, a calibration function for the Qmerit may be found. This calibration may also be applied on different target designs on the same layer. Similar target designs and methods may be applied to calculate the crosstalk-induced OVL error due to additional layer(s) which are not part of the alignment (for example: intra layer with dummy structures). It can also be used to estimate alignment mark errors. In certain embodiments, any of periodic structures 110, 120 may be replaced by respective features 110, 120 may be single non-segmented elements, such as full squares. While not periodic, such features 110, 120, and may be used in a similar fashion as unresolved periodic structures 110, 120, for example, metrology algorithms may be applied to detect their centers, edges, etc., similarly to corresponding algorithms applied to unresolved periodic structures.

Figure 4:
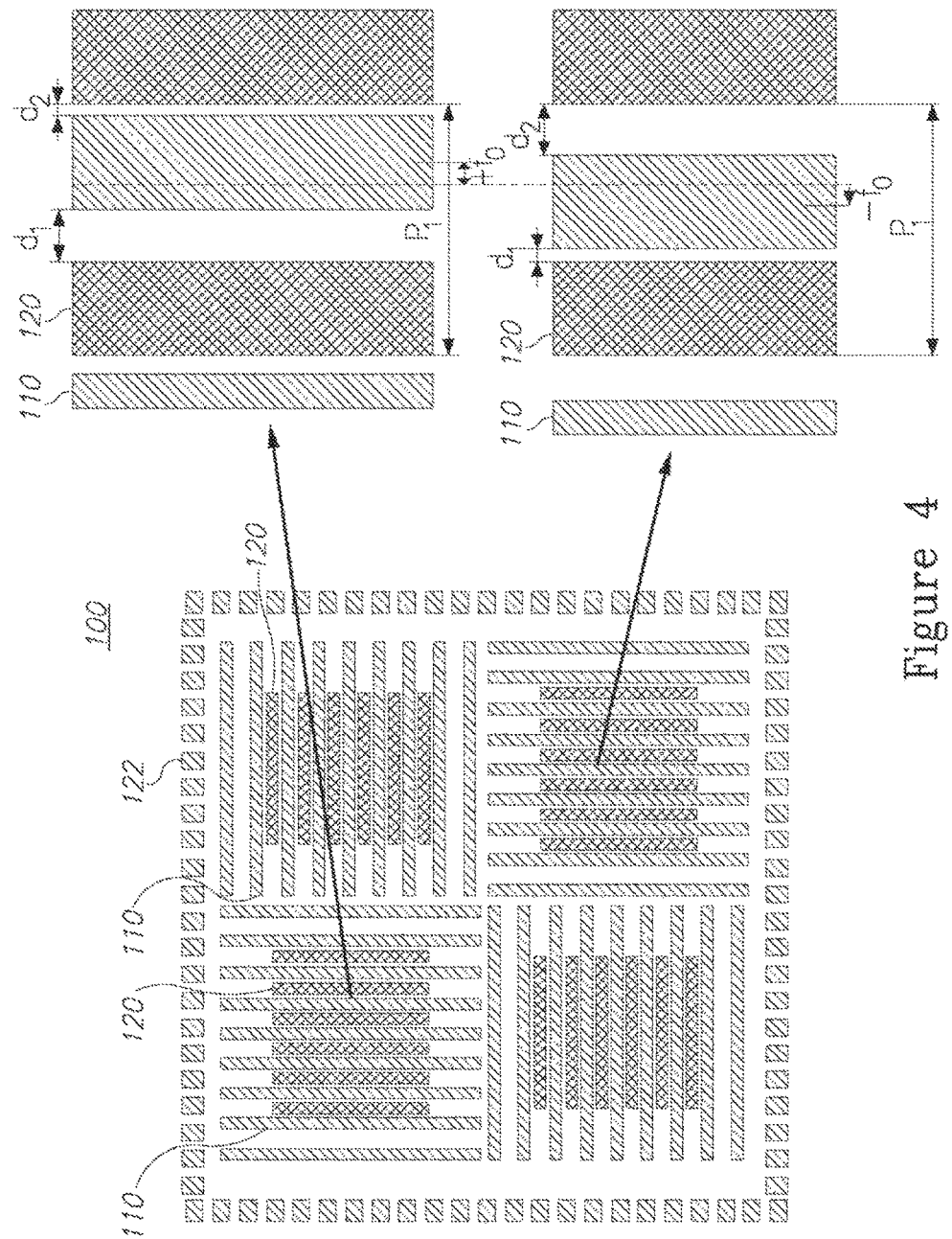
FIG. 4 is a high level schematic illustration of metrology targets, according to some embodiments of the invention.

FIG. 4 is a high level schematic illustration of metrology targets 100, according to some embodiments of the invention. The left side of FIG. 4 schematically illustrates a top view of target 100, having four cells (quarters of target 100 in the non-limiting illustration), two cells configured to enable metrology measurements in one direction and two cells configured to enable metrology measurements in another direction, similarly to target 100 illustrated in FIG. 1. A frame 122 may be added to target 100 to enhance positioning accuracy. The right side of FIG. 4 schematically illustrates enlarged top views of the target cells. Target 100 is illustrated, in a non-limiting manner, as having two layers, a bottom previous layer with periodic structure 110 and a top current layer with periodic structure 120. These layers may represent any number of target layers and may be interspaced by any number of intermediate layers.

In the illustrated case parallel periodic structures 110, 120 are completely non-overlapping, and the relation between respective structure pitches and the predetermined offsets are selected to leave specified gaps between adjacent target elements of parallel periodic structures 110, 120. As illustrated for one measurement direction, pitch $p_1$ and offsets $\pm f_0$ may be selected to leave gaps $d_1$, $d_2$ between adjacent target elements. The extent of overlapping between parallel periodic structures 110, 120 may be similar or different when compared to cells in different measurement directions. In certain embodiments, a difference in the degree of overlapping may vary between cells in the same measurement direction. Target 100 illustrated in FIG. 4 may be unresolved for imaging purposes along at least one measurement direction (e.g., $d_1$, $d_2$ smaller than illumination wavelength), as discussed above regarding FIG. 3.

Parallel periodic structures 110, 120 may differ in at least one of their dimensions. For example, as illustrated in FIG. 3, periodic structure 120 may have shorter target elements than periodic structure 110. Clearly, the differences in dimensions may be opposite (target elements of structure 110 being shorter than target elements of structure 120), or vary between measurement directions and/or cells. Other dimensions may vary in size between structures 110, 120, such as the width of the target elements. Target elements of periodic structures 110, 120 may be segmented, and segmentation characteristics (e.g., segmentation pitch, segment dimensions) may vary between structures 110, 120.

Figure 5:
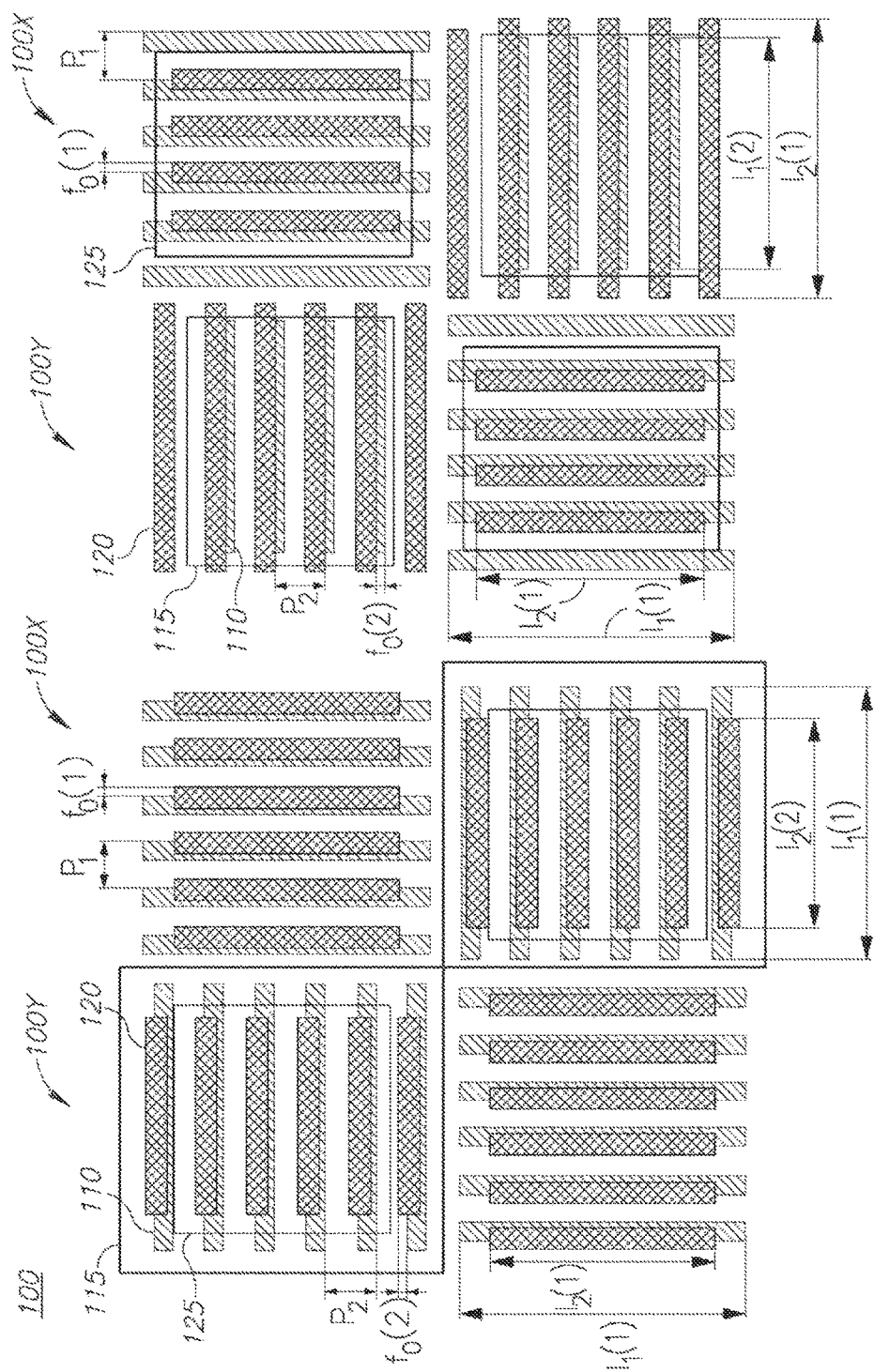
FIG. 5A is a high level schematic illustration of metrology targets and region of interest (ROI) selection, according to some embodiments of the invention.
FIG. 5B is a high level schematic illustration of metrology targets and region of interest (ROI) selection, according to some embodiments of the invention.

FIGS. 5A and 5B are high level schematic illustrations of metrology targets 100 and ROI selection, according to some embodiments of the invention. FIGS. 5A and 5B illustrate in a non-limiting manner, dimensional variation among parallel periodic structures 110, 120. For example, in FIG. 5A, periodic structures 120 are shorter than periodic structures 110 ($l_2(1) < l_1(1)$ in cells 100X and $l_2(2) < l_1(2)$ in cells 100Y), and are partially overlapping, while in FIG. 5B, periodic structures 120 are shorter than periodic structures 110 in the X measurement direction, i.e., in cells 100X, and are longer than periodic structures 110 in the Y measurement direction, i.e., in cells 100Y ($l_2(1) < l_1(1)$ in cells 100X and $l_2(2) > l_1(2)$ in cells 100Y), and are partially overlapping.

FIGS. 5A and 5B further illustrate selection of the regions of interest (ROI's 115, 125) for imaging measurements in the target designs. ROI's 115, 125 may be selected with respect to dimensions of respective periodic structures 110, 120 which are imaged. For example, ROI's 115, 125 may be selected to include respective imaged periodic structures 110, 120 and exclude target elements of periodic structures 120, 110 (respectively) which are outside the area of the acquired structure. For example, ROI 125 at the top right quarter of target 100 illustrated in FIG. 5B encloses periodic structure 120 and its immediate surroundings and excludes target elements of periodic structure 110 which extend beyond the region occupied by periodic structure 120. Hence, shortening some of the periodic structures may enable measurements of the layer feature edges which may be used to derive additional information regarding the layer's center of symmetry. In some configurations it enables overlay calculation using standard algorithms (when the crosstalk between the different layer feature edges is negligible). The difference between the center of symmetry as extracted from a measurement algorithm taking into account the asymmetric structure of the target (e.g., Qmerit) and the center of symmetry as extracted from a standard algorithm (assuming symmetric targets) may be calculated and used to estimate using a different approach the target's asymmetry. Another possibility is to use a CD to space ratio (i.e., the ratio between target element widths and the widths between target elements) different than one. Any parameters of periodic structures 110, 120 and target 100, such as intended shifts (predetermined offsets), coarse pitches ($p_1$, $p_2$), target element dimensions ($l_1$, $l_2$), segmentation CD and pitch, and direction and other target design parameters may be optimized to provide better results and enhance the synergy in using both imaging and scatterometry techniques on targets 100.

FIGS. 4 and 5A/5B implement similar design principles for different target configurations, namely bar over trench and bar over bar designs, respectively. The measurement of any of the target designs as resolved or unresolved elements depends on the selection of element dimensions, pitches and offsets, which may be carried out according to metrology specifications.

Figure 6:
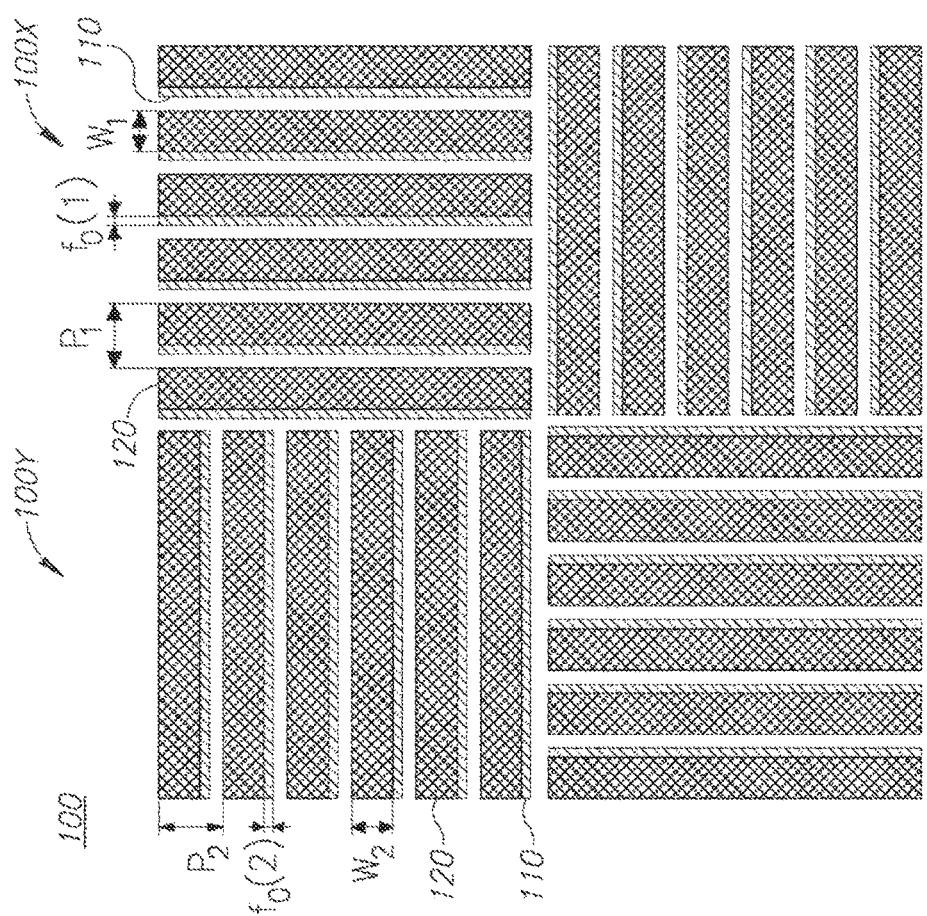
FIG. 6 is a high level schematic illustration of a metrology target, according to some embodiments of the invention.

FIG. 6 is a high level schematic illustration of metrology target 100, according to some embodiments of the invention. In the illustrated top view, parallel periodic structures 110, 120 are largely overlapping, having relatively small predetermined offsets (±f₀(1) and ±f₀(2)). Widths $w_1$ and $w_2$ of the target elements in periodic structures 110, 120 may be selected to optimize imaging and scatterometry performance.

Figure 7:
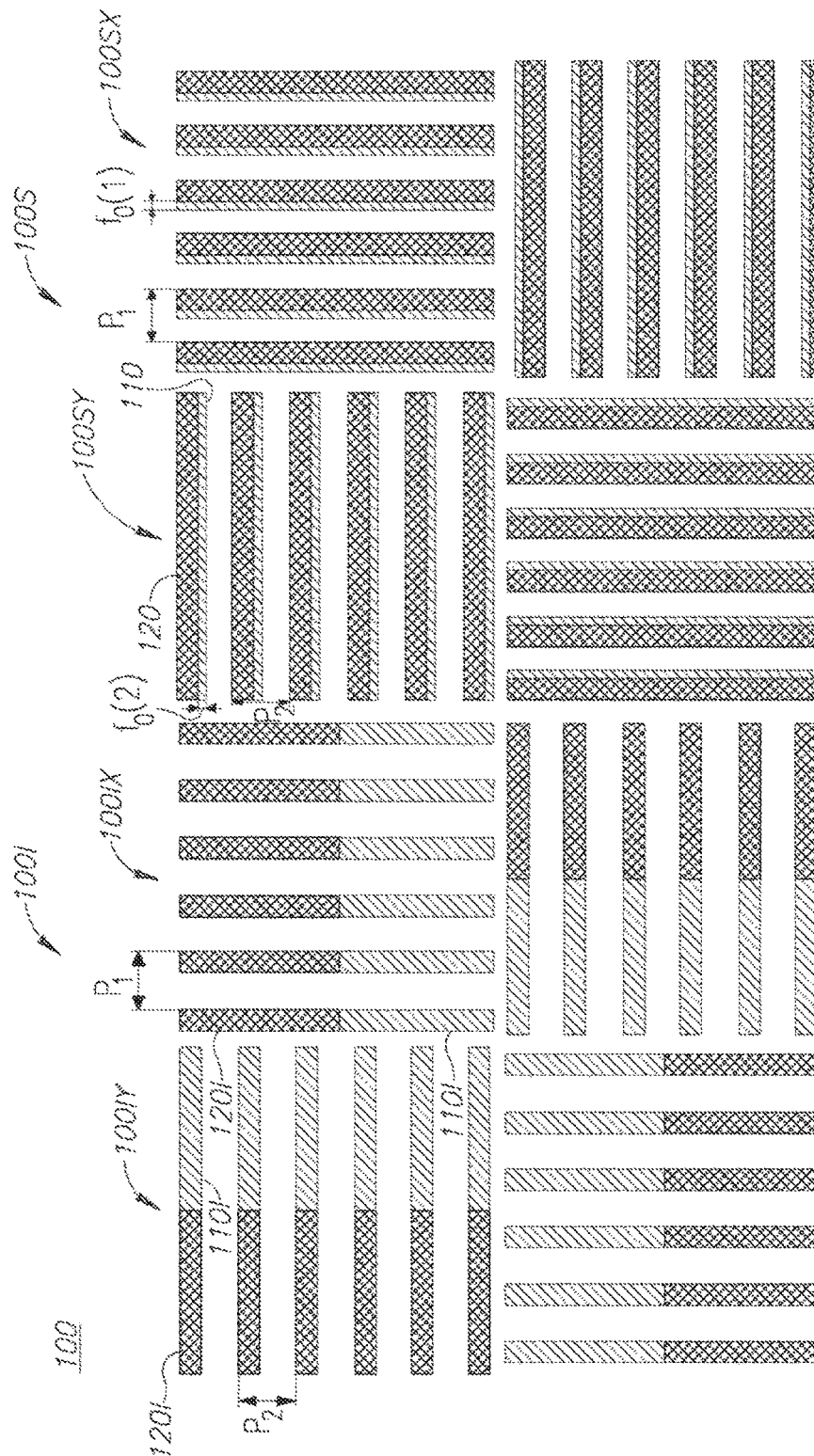
FIG. 7 is a high level schematic illustration of metrology targets having imaging and scatterometry parts, according to some embodiments of the invention.
Figure 8:
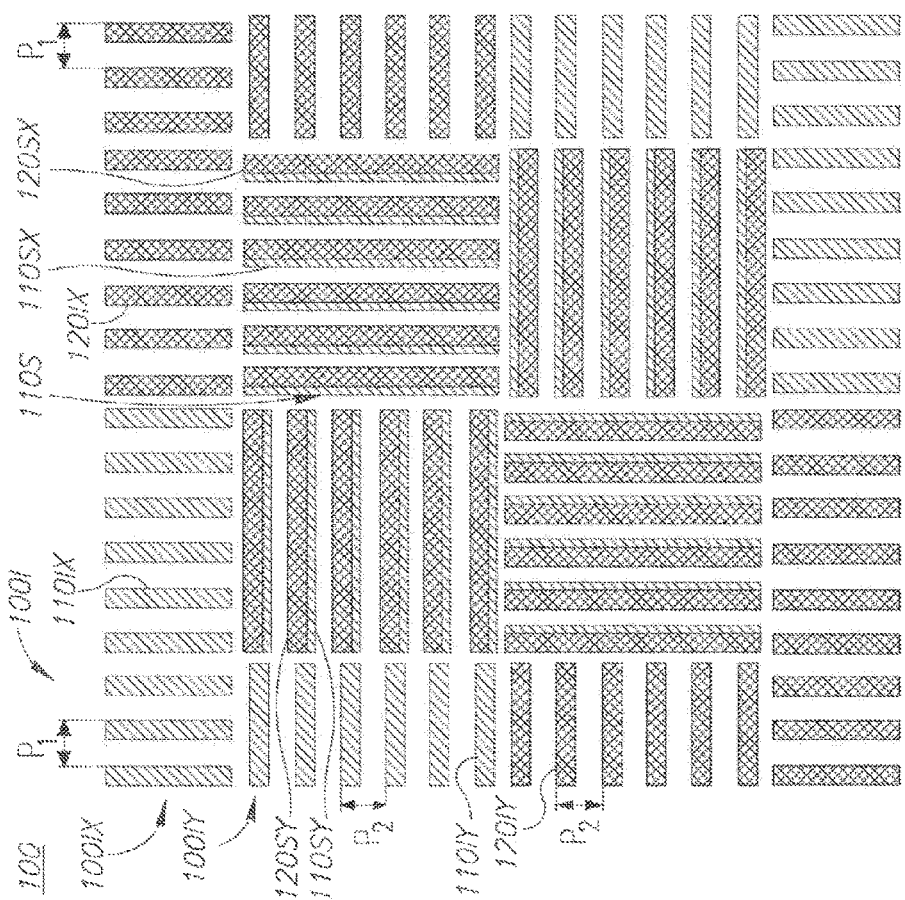
FIG. 8 is a high level schematic illustration of metrology targets having imaging and scatterometry parts, according to some embodiments of the invention.

FIGS. 7 and 8 are high level schematic illustrations of metrology targets 100 having imaging and scatterometry parts 100I, 100S respectively, according to some embodiments of the invention. Targets 100 may be configured to have a scatterometry part 100S with the at least two parallel periodic structures 110, 120 having the predetermined offset therebetween, and an imaging part 100I lacking the predetermined offset. FIG. 7 illustrates imaging part 100I adjacent to scatterometry part 100S; FIG. 8 illustrates imaging part 100I enclosing scatterometry part 100S. Target elements in scatterometry part 100S and in imaging part 100I may share at least one dimension.

A illustrated in FIG. 7, cells 100SX, 100SY in two measurement directions of scatterometry part 100S may comprise parallel periodic structures 110, 120 having predetermined offsets therebetween. Cells 100SX, 100SY may have similar or different pitches $p_1$, $p_2$ and offsets $f_0(1, 2)$. Cells 100IX, 100IY in two measurement directions of imaging part 100I may comprise periodic structures 110I, 120I, which may be parallel or respectively continuous, and configured according to imaging requirements. At least some dimensions of periodic structures 110I, 120I may be similar to dimensions of periodic structures 110, 120 in scatterometry part 100S, while other dimensions may differ. For example, in the non-limiting illustrated case, pitches $p_1$, $p_2$ and target element widths may be similar while target element lengths may differ.

As illustrated on the left side of FIG. 8, the cells in two measurement directions of scatterometry part 100S, which is in the illustrated case enclosed within imaging part 100I, may comprise parallel periodic structures 110SX, 120SX, 110SY, 120SY having predetermined offsets therebetween. The cells may have similar or different pitches $p_1$, $p_2$ and offsets. Cells 100IX, 100IY in two measurement directions of imaging part 100I, configured to enclose scatterometry part 100S, may comprise periodic structures 110IX, 120IX, 110IY, 120IY, which may be arranged to enclose scatterometry part 100S, e.g., by forming a frame around its periphery, and be configured according to imaging requirements. At least some dimensions of the target elements in imaging part 100I may be similar to dimensions of target elements in scatterometry part 100S, while other dimensions may differ. For example, in the non-limiting illustrated case, pitches $p_1$, $p_2$ and target element widths may be similar while target element lengths may differ.

In any of the target designs, dimensions of parallel periodic structures 110, 120 may be selected to comply with requirements for both imaging and scatterometry measurements. In any of the target designs, target elements of periodic structures 110, 120 may be segmented to comply with production requirements, e.g., comply with design rules, as well as with the requirements for both imaging and scatterometry measurements. In any of the target designs, background regions of target elements of periodic structures 110, 120 may be segmented to comply with production requirements, e.g., comply with design rules, as well as with the requirements for both imaging and scatterometry measurements.

Figure 9:
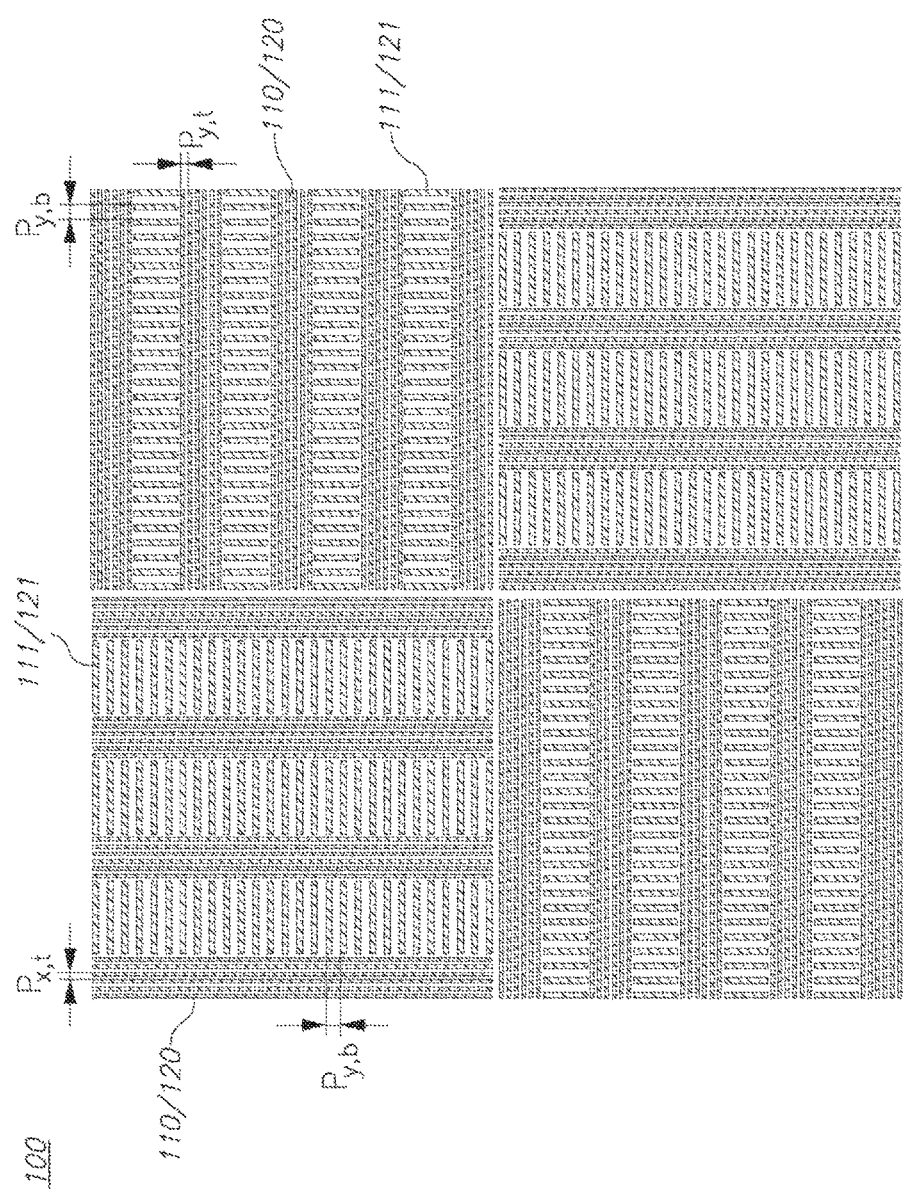
FIG. 9 is a high level schematic illustration of a segmented metrology target layer, according to some embodiments of the invention.

FIG. 9 is a high level schematic illustration of segmented metrology target layer 100, according to some embodiments of the invention. The segmentation may be applied to whole target 100 or to parts of target 100, e.g., to scatterometry part 100S. Periodic structures 110, 120 in any part of target 100, and/or their respective background regions 111, 121 in any of the target layers may be segmented in directions that maintain or enhance imaging and/or scatterometry measurements. Measurement algorithms and optics may be adjusted to enhance imaging and/or scatterometry results of targets 100 (e.g., use polarized light, compare imaging and scatterometry measurements etc.). Some regions of target 100 may be segmented while others may be left blank, e.g., scatterometry part 100S may be segmented while imaging part 100I may be unsegmented or vice versa. Measurement considerations regarding each of parts 100I, 100S may be used to determine the form of segmentation, e.g., imaging contrast and diffraction pattern features, respectively. Segmented target 100 may be measured with polarized light to enhance contrast and resolution of either or both imaging and scatterometry measurements. In the illustrated example, target elements 110/120 (the double notation relates to target elements in lower/upper (previous/current) layer respectively), may be segmented with pitch $p_{x,t}$ in the x measurement direction and with pitch $p_{y,t}$ in the y measurement direction, wherein the pitches in the different directions may differ. Similarly, backgrounds 111/121 (referring to backgrounds in lower/upper layer respectively) may be segmented vertically to target elements 110/120 with respective pitches $p_{x,b}$, $p_{y,b}$ which may be different or similar. Different patterns may be applied to segmentation of target elements 110/120 and/or backgrounds 111/121. The target design of FIG. 9 may be implemented in one or more of the layers in metrology target 100.

FIGS. 10A-10C are high level schematic illustrations of metrology targets 100, according to some embodiments of the invention. FIGS. 10A-10C illustrate targets 100 having parallel periodic structures 110, 120 which differ in pitch p and/or element width w. FIG. 10A schematically illustrates a top view of target 100 having periodic structure 120 with wider elements and larger pitch than periodic structure 110. Similarly to FIG. 3, some of the target features may be unresolved in imaging measurements yet be used to enhance respective scatterometry measurements. FIGS. 10B and 10C schematically illustrate cross sections of two configurations of parallel periodic structures 110, 120, namely with pitches and element widths of $p_1$, $w_1$ and $p_2$, $w_2$, respectively. In both cases the predetermined offsets are denoted by $f_0$. It is noted that target 100 of FIG. 10B is designed to have partial area coverage (in top view) by periodic structures 110, 120 while that target 100 of FIG. 10C is designed to have full area coverage (in top view) by periodic structures 110, 120, making the periodic structures in the latter unresolved along the measurement direction using imaging measurements. Periodic structure 110 in FIGS. 10A, 10B may be designed to be unresolved while periodic structure 120 in may be designed to be resolved in the metrology measurements.

Figure 11:
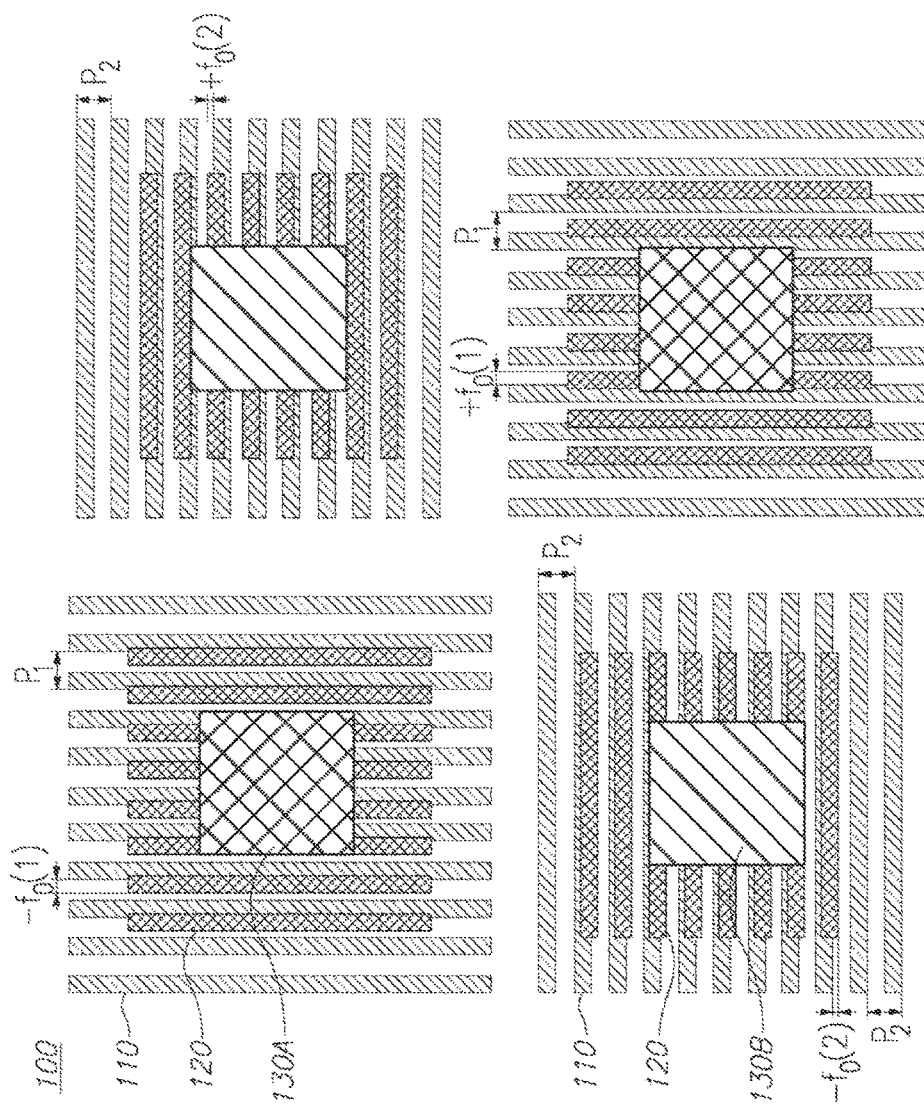
FIG. 11 is a high level schematic illustration of a multi-layered metrology target, according to some embodiments of the invention; and, FIG. 12 is a high level flowchart illustrating a method, according to some embodiments of the invention.

FIG. 11 is a high level schematic illustration of multi-layered metrology targets 100, according to some embodiments of the invention. FIG. 11 illustrates targets 100 having target elements 130A, 130B in additional layers above (or below or intermediate between) parallel periodic structures 110, 120. Overlays between one or both layers of target elements 130A, 130B and periodic structures 110, 120 may be measured using imaging techniques. Target elements 130A, 130B may comprise periodic structures which are parallel or perpendicular of periodic structures 110, 120 and respective predetermined offsets may be introduced between any pair of periodic structures. Target elements 130A, 130B may be segmented. Imaging and/or scatterometry measurements may be used to measure any combination of the layers.

Certain embodiments of the disclosed invention comprise any of imaging measurements, scatterometry measurements, a combination thereof and imaging-enhanced scatterometry measurements of any of targets 100 and their variants. Furthermore, certain embodiments of the disclosed invention comprise target design files of any of targets 100 and their variants.

In certain embodiments, in order to improve the imaging signal to noise ratio, the zero order of the reflected light may be attenuated or blocked. In addition to overlay measurements, targets 100 may be designed to enable measurements of other metrology parameters, such as CD-SEM (scanning electron microscopy imaging of critical dimensions) using respective measurement techniques and metrics.

The inventors have found out that combining data from imaging and scatterometry measurement techniques applied to the same targets significantly enhances metrology measurements, such as overlay measurements. While optical crosstalk between different layers is, in the prior art, a major constraint in overlay target design, the disclosed target designs overcome this issue, estimate the extent of crosstalk and utilize the crosstalk to measure the overlay more accurately and/or using smaller targets. In order to estimate the overlay error that induced by layer crosstalk targets 100 are designed with induced shifts (predetermined offsets) between the current and the previous layer, having respective periodic structures. Furthermore, the combination of different measurement techniques may be used to extract the overlay and additional process information. For example, the scatterometry may provide information about layer thickness variations while the imaging provides information about the side wall angle. This can be used to extract additional data about the target shape and process variations.

Figure 12:
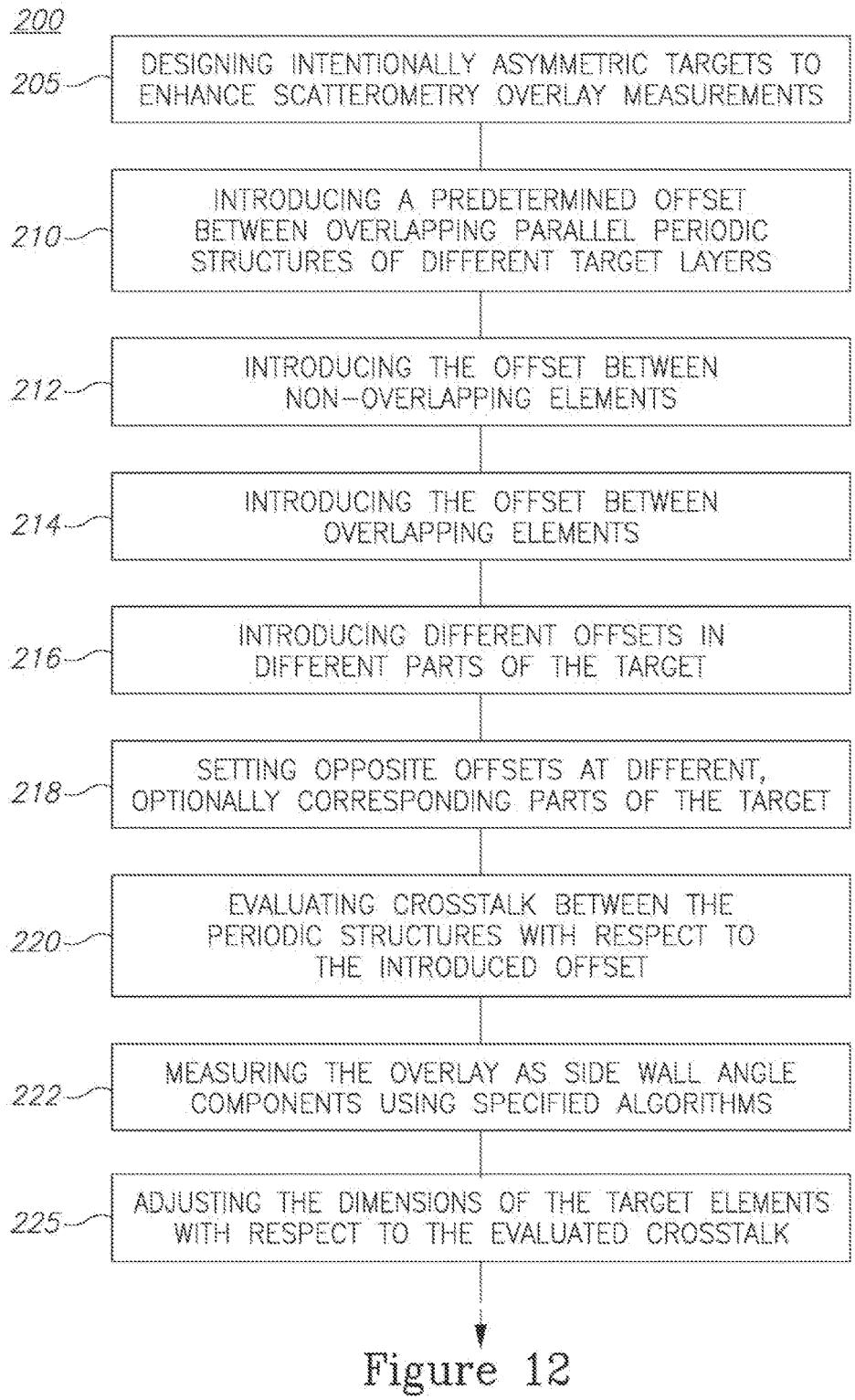

FIG. 12 is a high level flowchart illustrating a method 200, according to some embodiments of the invention. Method 200 may comprise stages for designing and/or producing targets 100, as well as configuring respective target design files. Method 200 may further comprise measurement stages of targets 100. Method 200 may comprise any of the following stages, irrespective of their order.

Method 200 may comprise designing intentionally asymmetric targets to enhance scatterometry overlay measurements (stage 205) and/or introducing a predetermined offset between overlapping parallel periodic structures of different target layers (stage 210). Stage 210 may comprise introducing the offset between non-overlapping elements, such as parallel periodic structures (stage 212) and/or introducing the offset between overlapping elements, such as parallel periodic structures (stage 214).

Method 200 may further comprise introducing different offsets in different parts of the target (stage 216), for example setting opposite offsets at different, optionally corresponding parts of the target (stage 218). In certain embodiments, the opposite predetermined offsets add differently to unintentional overlays and thus allow extracting the unintentional overlays from differences in overlay measurements by different algorithms. In certain embodiments, method 200 may further comprise measuring targets wherein at least one of the periodic structures is unresolved under specified measurement conditions and/or wherein at least one of the periodic structures comprises a single target element.

Method 200 may comprise measuring a metrology parameter using different algorithms (stage 230), e.g., obtaining imaging overlay measurements using different algorithms (stage 232); estimating the target asymmetry using the difference in measurement results obtained by the different algorithms (stage 235), e.g., by processing a difference between results of a same metrology parameter by at least two alternative algorithms (stage 240) or generally applying a quality measure to the difference between the algorithms to estimate the target asymmetry and derive the unintentional offset therefrom (stage 245).

Method 200 may further comprise evaluating crosstalk between the periodic structures with respect to the introduced offset (stage 220) and adjusting the dimensions of the target elements with respect to the evaluate cross talk (stage 225). In certain embodiments, stage 220 may comprise measuring the overlay as side wall angle components using specified algorithms (stage 222). In certain embodiments, stage 220 may comprise designing one or more periodic structures to be unresolved elements in imaging measurements (stage 227).

Method 200 may comprise designing intentionally asymmetric targets to provide imaging and scatterometry measurements simultaneously (stage 250) and adjusting the dimensions of the target elements to optimize the simultaneous imaging and scatterometry measurements (stage 255). Method 200 may comprise combining and coordinating imaging structures and scatterometry structures into a single hybrid target (stage 260). Method 200 may for example comprise designing the hybrid target to have adjacent imaging and scatterometry parts (stage 262) or designing the hybrid target to have an imaging part enclosing a scatterometry part (stage 264). Method 200 may comprise any of the following stages: using imaging measurements to enhance scatterometry measurements (stage 270), comparing measured quantities between the imaging and scatterometry measurements (stage 272) and configuring measurement conditions to optimize the utilization of the simultaneous imaging and scatterometry measurements (stage 274). Comparison 272 may further comprise any of the following: comparing imaging and scatterometry measurements, enhancing one of imaging and scatterometry measurements by the other, and selecting imaging and scatterometry measurements according to temporal or spatial requirements. In certain embodiments, method 200 may further comprise deriving information regarding process and target quality and defects by combining overlay values and quality merits of both imaging and scatterometry measurements. Method 200 may further comprise improving process monitoring and/or process control using the derived information.

Method 200 may further comprise configuring the metrology target to have a scatterometry part with the at least two parallel periodic structures having the predetermined offset therebetween, and an imaging part lacking the predetermined offset. Method 200 may comprise designing at least some of the target elements in the scatterometry part and in the imaging part to share at least one dimension. Method 200 may comprise using similar target elements for both imaging and scatterometry parts (stage 266).

Method 200 may comprise introducing a predetermined offset between at least two parallel periodic structures at respective layers of a metrology target, e.g., at a scatterometry part of the target only (stage 265). Method 200 may comprise selecting dimensions of the at least two parallel periodic structures to comply with requirements for both imaging and scatterometry measurements and configuring respective target parameters to enable both imaging and scatterometry measurements. Method 200 may comprise configuring the at least two parallel periodic structures to have at least one different dimension and selecting an imaging region of interest (ROI) as an area in which the at least two parallel periodic structures are at least partially overlapping.

Method 200 may comprise any of the following stages: segmenting at least some of the target elements of the periodic structures (stage 280), segmenting background regions of at least some target element of the periodic structures and providing target elements in additional layers (stage 285).

Method 200 may further comprise producing respective target design files and targets (stage 290), carrying out any of the designing and calculation by a computer processor (stage 292) and carrying out metrology measurements of the produced targets (stage 294), e.g., using polarized light for at least some of the measurements (stage 295). Method 200 may further comprise attenuating or blocking a zero order reflection during at least some of the measurements, e.g., to enhance overlay detection using first or higher order scatterometry patterns.

Advantageously, with respect to prior art such as U.S. Patent Publication No. 2013/0208279 which discloses image based overlay measurements performed using an overlay target that includes shifted overlying gratings, the current disclosure combines imaging and scatterometry target structures, provides simultaneous or sequential measurements of the target using both imaging and scatterometry techniques, optimizes target structures with relation to the requirements of both techniques, and further discloses mutual enhancement of measurement results through the combination of the measurement methods. As explained above, targets 100 allow flexible selection and configuration of the specific measurement techniques and the disclosure further provides a wide range of measurement processing embodiments which may be used to optimize the extraction of useful information from the target measurements, with respect to given requirements. Furthermore, disclosed methods 200 enable deriving metrology measurements from, and applying of metrology algorithms to, both resolved and unresolved target elements, structures and features. In particular, measuring unresolved features enables reducing the size of the smallest target elements to be close to or even reach the dimensions of device elements, thus making metrology targets more reliable in representing device features and less prone to process associated inaccuracies resulting from their larger dimensions.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology target comprising:
a first layer and at least a second layer, wherein the at least the second layer is positioned above at least a portion of the first layer;
a scatterometry part configured for obtaining scatterometry measurements, wherein the scatterometry part includes:
two or more target cells, wherein at least some target cells of the two or more target cells includes a first set of periodic structures formed in the first layer and a second set of periodic structures formed in the at least the second layer,
wherein adjacent periodic structures in the first set of periodic structures are separated by a first selected pitch,
wherein adjacent periodic structures in the second set of periodic structures are separated by a second selected pitch,
wherein a periodic structure in the first set of periodic structures is separated from a corresponding periodic structure in the second set of periodic structures by a predetermined offset; and
an imaging part configured for obtaining imaging measurements, wherein the imaging part includes:
a third set of periodic structures formed in the first layer and at least a fourth set of periodic structures formed in the at least the second layer,
wherein the third set of periodic structures and the at least the fourth set of periodic structures are proximate to the two or more target cells,
wherein a periodic structure of the third set of periodic structures and a periodic structure of the at least the fourth set of periodic structures are not separated by a predetermined offset.

2. The metrology target of claim 1, wherein a first target cell of the two or more target cells includes a different predetermined offset than at least a second target cell of the two or more target cells.

3. The metrology target of claim 1, wherein a first target cell of the two or more target cells includes an opposite predetermined offset than at least a second target cell of the two or more target cells.

4. The metrology target of claim 1, wherein the two or more target cells are configured with at least one of a selected pitch or a predetermined offset usable for both obtaining one or more imaging measurements and obtaining one or more scatterometry measurements.

5. The metrology target of claim 1, wherein the two or more target cells include a first target cell and at least a second target cell, wherein a predetermined offset between a periodic structure in a first set of periodic structures and a corresponding periodic structure in at least a second set of periodic structures in the first target cell is opposite in direction from a predetermined offset between a periodic structure in a first set of periodic structures and a corresponding periodic structure in at least a second set of periodic structures in the at least the second target cell.

6. The metrology target of claim 1, wherein a periodic structure in the first set of periodic structures and the corresponding periodic structure in the second set of periodic structures within at least some target cells of the two or more target cells are at least partially overlapping.

7. The metrology target of claim 1, wherein a periodic structure in the first set of periodic structures and the corresponding periodic structure in the second set of periodic structures within at least some target cells of the two or more target cells are non-overlapping.

8. The metrology target of claim 1, wherein the first selected pitch between adjacent periodic structures in the first set of periodic structures is equal to the second selected pitch between adjacent periodic structures in the at least the second set of periodic structures within at least some target cells of the two or more target cells.

9. The metrology target of claim 1, wherein the first selected pitch between adjacent periodic structures in the first set of periodic structures differs in at least one dimension from the second selected pitch between adjacent periodic structures in the at least the second set of periodic structures within at least some of the target cells of the two or more target cells.

10. The metrology target of claim 1, wherein at least one of the first set of periodic structures or the at least the second set of periodic structures within at least some target cells of the two or more target cells are unresolved under specified measurement conditions, wherein the specified measurement conditions are dependent on a pitch size of a set of periodic structures relative to an illumination wavelength.

11. The metrology target of claim 1, wherein at least one periodic structure of the first set of periodic structures and a corresponding periodic structure of the at least the second set of periodic structures within at least some target cells of the two or more target cells form a single target element.

12. The metrology target of claim 1, wherein at least one of a selected pitch or a predetermined offset within at least some target cells of the two or more target cells are selected to comply with requirements for both obtaining one or more imaging measurements and obtaining one or more scatterometry measurements.

13. The metrology target of claim 1, wherein the imaging part is adjacent to the scatterometry part.

14. The metrology target of claim 1, wherein the imaging part encloses the scatterometry part.

15. The metrology target of claim 1, wherein target elements in the scatterometry part and in the imaging part share at least one dimension.

16. The metrology target of claim 1, wherein at least one target element formed by at least one periodic structure of the first set of periodic structures and a corresponding periodic structure of the at least the second set of periodic structures within at least some target cells of the two or more target cells are segmented.

17. The metrology target of claim 1, wherein at least a background region of at least one target element formed by at least one periodic structure of the first set of periodic structures and a corresponding periodic structure of the at least the second set of periodic structures within at least some target cells of the two or more target cells are segmented.

18. The metrology target of claim 1, wherein the metrology target is configured to be stored in memory in the form of a metrology target design file.

* * * * *